United States Patent [19]

Turner et al.

[11] Patent Number: 4,846,945

[45] Date of Patent: Jul. 11, 1989

[54] OXIDATION PROCESS

[75] Inventors: Philip J. Turner, Widnes; Vincent I. Routledge, Warrington; Martin Jeff, Frodsham, all of England

[73] Assignee: Interox Chemicals Limited, London, England

[21] Appl. No.: 92,362

[22] Filed: Sep. 2, 1987

[30] Foreign Application Priority Data

Sep. 6, 1986 [GB] United Kingdom ................. 8621519

[51] Int. Cl.$^4$ ........................ B01J 19/08; C07C 45/29; C07C 45/30
[52] U.S. Cl. .......................... 204/157.93; 204/157.94; 568/361; 568/362; 568/364; 568/403
[58] Field of Search ........... 204/157.15, 157.9, 157.93, 204/157.94; 568/361, 362, 364, 403

[56] References Cited

U.S. PATENT DOCUMENTS

| 2,674,572 | 4/1954 | Gundel | 204/157.93 |
| 3,701,722 | 10/1972 | Heckert | 204/157.93 |
| 3,985,808 | 10/1976 | Gutieriez | 568/361 |

FOREIGN PATENT DOCUMENTS 622686 6/1961 Canada ................................. 568/364

OTHER PUBLICATIONS

Venkatasubramanian, N., et al., "The Mechanism of Oxidation of Alcohols by Bromine", Dept. of Chemistry, Vivekanada College, Mylapore, Madras-4, India, pp. 1171–1714.
Swain, C. Gardner, et al., "Use of Substituent Effects on Isotope Effects to Distinguish between Proton and Hydride Transfers, Pt. I. Mechanism of Oxidation of Alcohols by Bromine in Water", *Oxidation of Alcohols by Bromine in Water*, Apr. 20, 1961, vol. 83, pp. 1945–1950.
Deno, N. C., et al., "The Mechanism of Oxidation of Alcohols by Aqueous Bromine", *Journal of the American Chemical Society*, 89:14/Jul. 5, 1967, pp. 3355–3356.
Barker, I. R. L., et al., "The Oxidation of Cyclohexanol and Related Compounds with Bromine", *J. Chem. Soc.*, 1964, pp. 3263–3267.

*Primary Examiner*—John F. Niebling
*Assistant Examiner*—Ben C. Hsing
*Attorney, Agent, or Firm*—Larson and Taylor

[57] ABSTRACT

Oxidation of alcohols to ketones using bromine suffers from a side reaction of comparable speed in which a bromide substituted product is formed. Additionally, the use of bromine as reagent is relatively unpleasant and it creates a major waste disposal problem.

The latter problem can be solved by generating bromine in situ by reaction between hydrogen peroxide and bromide ions or hydrogen bromide, but this inevitably increases the exposure of the alcohol to HBr/Br$^-$. The selectivity of the process towards non-substituted oxidation depending upon the inherent deactivation or reactivity of the alcohol can be improved by irradiating the reactants with light of suitable frequency to generate bromine radicals in the mixture, and/or by controlling the rate of introduction of the hydrogen peroxide and controlling the extent to which mole ratio of HBr:alcohol is substoichiometric. Selectivity can also be improved by employing a two-phase reaction mixture, the alcohol being present to a considerable extent in the organic phase with HBr/Bromide being retained to a great extent in the aqueous phase.

It is particularly beneficial for the selective oxidation of alcohols that are substituted by adjacent electronegative groups, for example chloropropanols.

26 Claims, No Drawings

OXIDATION PROCESS

BACKGROUND OF THE INVENTION

The present invention relates to an oxidation process particularly for alcohols and especially to the oxidation of a secondary alcohol to a ketone.

Various ketones are employed as chemical intermediates, for example in the synthesis of pharmaceuticals, one of which intermediates is 1,3-dichloroacetone. Currently, the ketone is produced by oxidation of the corresponding alcohol or chlorination of acetone, but both routes are subject to substantial practical problems. In the former route, there are difficulties of contamination of the product with the oxidant and the purification or other disposal of the effluent and in the latter route there is a severe risk of overchlorination, which inevitably reduces the purity and yield of the product.

In principal, there are many strong oxidants that might be expected to oxidise alcohols but they may also otherwise react with them and/or other substituents of the alcohol-containing molecule. One such oxidant comprises bromine. A paper by N. Venkatasubramanian and V. Thiagarajan in Tetrahedron Letters No. 14 pp 1711-1714 published by the Pergamon Press in London 1968 reviewed various possible mechanisms proposed for the bomine/alcohol reaction both by themselves and earlier by Deno and Potter in JACS 82, 406 (1967), Swain, Wiles and Bader in JACS 83, 1945 (1961) and Barker, Overenk and Rees in JCS 3263 (1964). The disclosure indicates that the presence of a strong electronegative substituent adjacent to the hydroxyl group retards the oxidation reaction considerably. On the other hand, it has also been recognised that ketones in particular are susceptible to bromine substitution reactions probably effected chemically by $HBr/Br^-$. The studies leading to the present invention confirm that the reaction products can include both ketone and brominated compounds.

Bromine itself as a reagent is particularly unpleasant to handle, especially on an industrial scale because it is a toxic low boiling point liquid that can react with water to form toxic and corrosive fumes. Moreover, the resultant hydrogen bromide reaction product, in theory twice the molar amount of bromine introduced, poses considerable and therefore expensive waste disposal problems. It would, at least in theory, be attractive to employ a technique of regenerating bromine from hydrogen bromide, because such a procedure would reduce the problems of handling bromine and disposing of hydrogen bromide, but it follows that such a technique would inevitably maximise the exposure of the alcohol/ketone to contact with $HBr/Br^-$ throughout the entire reaction period and accordingly increase the extent of the unwanted bromine substitution reactions.

SUMMARY OF THE INVENTION

It is an object of the present invention to promote the oxidation of alcohols with bromine, either in rate of oxidation or selectivity relative to competitive reactions, whilst generating the bromine in situ.

In the present invention process, the bromine is generated in situ by reaction between hydrogen peroxide and hydrogen bromide, despite the fact that adoption of such a procedure inevitably suffers from the competitive bromine substitution reactions, and the invention resides in the control of the process so as to favour the oxidation and/or disfavour the bromine substitution reactions.

DETAILED DESCRIPTION OF THE INVENTION

It has been found that attainment of improved product selectivity in the invention is assisted by the inventors recognition of two contributory factors and their manner of interaction. In one factor, which represents one aspect of the present invention, the reaction between the alcohol and bromine is effected by illuminating the reaction mixture with radiation that can dissociate bromine into free radicals. It has hitherto not been recognised that bromine radicals play a significant role in the oxidation of at least some alcohol oxidation. By increasing the generation of free radicals by irradiation of the bromine, the oxidation rate can thereby be accelerated and it has also been found that the selectivity of the process is also improved. In the second factor, which represents the second aspect of the instant invention, the reaction between bromine and an alcohol is effected in such a manner as to reduce the interaction between the alcohol reactants and product and $HBr/Br^-$, particularly by controlling the rate of generation of bromine in situ and preferably in addition by carrying the reaction out in a two phase system, one phase being relatively polar and the other phase being relatively nonpolar, whereby the organic reactant and products are retained preferentially in the non-polar phase whereas the inorganic product, $HBr/Br^-$ is retained preferentially in the polar phase. As a result of separating the inorganic and organic products, the bromination side reactions can be restricted, thereby improving the selectivity of the reaction.

It has been recognised by the inventors that the relative importance of the two factors depends to a substantial extent upon the inherent reactivity of the alcohol. Expressed as a generalisation, the extent to which the first factor affects the outcome of the competetion between the desired oxidation and non-desired bromination reactions increases in line with the extent of deactivation of the alcohols. On the other hand, if a reactive alcohol is employed, then the first factor assumes little importance and the second factor becomes dominant. Subject to the foregoing, it is particularly beneficial to employ a process incorporating both factors, that is to say irradiating appropriately a two phase reaction mixture.

In accordance with the foregoing, there is provided a process for the oxidation of a secondary alcohol to a ketone by reacting it with at least a stoichiometric amount of bromine characterised by employing, regenerating and reemploying in the reaction mixture a substoichiometric amount of hydrogen bromide in a two step cycle in which in one step of said cycle bromine is generated in situ by reaction between the bromide and hydrogen peroxide and in the second step of said cycle bromine is consumed by reaction with the alcohol with consequential regeneration of bromide and further characterised in that one of features (a) or (b) is employed essentially and the other optionally, the selection being dependent upon the inherent reactivity of the alcohol with bromine, (a) being essential when the alcohol is deactivated and (b) becoming progressively essential as the alcohol to be oxidised becomes comparatively more active, feature (a) comprising irradiating the reaction mixture with radiation that is capable of dissociating bromine into free radicals, and feature (b) comprising the use of a comparatively rapid rate of introduction of the hydrogen peroxide in conjunction with a comparatively restricted sub-stoichiometric mole ratio of HBr:alcohol in the reaction mixture, whereby the selectivity of the reaction is improved.

The invention can be employed in respect of secondary aliphatic alcohols as a class, and also cycloaliphatic alcohols such as cyclohexanol and aryl-substituted aliphatic alcohols including benzoin, taking into appropriate account the extent to which of the two factors is dominant. Thus, when the invention process is employed to oxidise saturated alcohols which are substituted on carbon atoms adjacent to the hydroxyl-substituted carbon atom by deactivating, viz electronegative substituents, particularly halogens such as chloride, and indeed it is especially suited to oxidising more selectively those alcohols, the most important aspect is the promotion of bromine radicals by appropriate radiation. Thus, the invention is readily applicable to the oxidation of chloro-aliphatic alcohols, if they are secondary. In the case of secondary alcohols either or both of the adjacent carbons can be halogen substituted. The number of carbon atoms in the alcohol is often 10 or less and is at least 3. One alcohol of especial interest is 1,3-dichloropropan-2-ol, in that its oxidation to 1,3-dichloroacetone can be effected readily whilst minimising halo-substitution or other side reactions. Further halo-sustituted alcohols of interest are 1,1,1-trichloropropan-2-ol and dibromopropanol.

In the case of relatively reactice alcohols, such as cyclohexanol and to a somewhat lesser extent nonsubstituted saturation aliphatic secondary alcohols, like 2-hexanol or 2-octanol, the importance of generating bromine radicals for the reaction is markedly reduced, and in the extreme even to insignificance, whereas the control of HBr/Br$^-$ becomes very significant.

The reaction is most conveniently carried out with the alcohol in a non-aqueous solution. When the liquid solvent is a single phase, it is desirable to use a liquid hydrocarbon or halogenated (especially chlorinated) hydrocarbons. The presently preferred solvent is chloroform but other such as ethylene dichloride and dichloromethane are useful alternatives. Mixtures of the organic solvents are usable also. These fractions of halogenated hydrocarbon solvents or mixtures thereof are preferred which have boiling points of around 50 to 100° C. It will be recognized that they can be augmented by mixture with water, a polar solvent, to form a 2 phase liquid system, which represents the second aspect of the present invention. The concentration of alcohol reactant in the organic solvent is often from 100 to 300 gpl.

The desired overall oxidation reaction is:

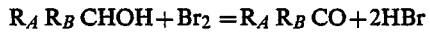

$R_A R_B CHOH + Br_2 = R_A R_B CO + 2HBr$

Thus, the stoichiometric amount of bromine is one mole of bromine per mole of alcohol, and conveniently from 1 to 3 moles Br$_2$ per mole alcohol. Whilst the overall generation of bromine is greater than one mole per mole of alcohol, at most only part of it is generated before the process commences.

Accordingly a substantially substoichiometric amount of hydrogen bromide can be employed and effectively recycled through several oxidations provided that at least a stoichiometric amount of hydrogen peroxide is employed. The relevant bromine generation reaction is:

$H_2O_2 + 2HBr = Br_2 + 2H_2O$, i.e. one mole of hydrogen peroxide theoretically can generate one mole of bromine, so that a stoichiometric amount of hydrogen peroxide is 1 mole per mole of alcohol. In practice, the relative amounts of HBr and alcohol to employ take into account the reactivity of the alcohol. Expressed in broad terms, the more reactive alcohols can tolerate or even benefit from a comparatively low ratio of HBr:alcohol, whereas for alcohols of lesser reactivity, it is preferable to use a somewhat higher HBr:alcohol ratio, though still substoichiometric. For alcohols of lesser reactivity, ie those containing at least one deactivating substituent on the alpha carbon atom to the hydroxyl-substituted carbon atom, it is convenient to use at least 0.4 moles of HBr and preferably at least 0.7 moles HBr per mole alcohol. Although a higher mole ratio could be used, it is generally not above 2:1 and often up to 1.5:1 moles HBr:alcohol. For the more reactive alcohols, ie those that are not so substituted, the ratio is normally at least 0.05 moles of HBr and often selected in the range of from 0.1 to 1.5 moles HBr per mole of alcohol. For these more reactive alcohols, the selection takes into account the fact that selectivity increases as the mole ratio decreases, but there is a concomitant tendency for yield to decrease also, which may be ameliorated by employing a correspondingly higher amount of hydrogen peroxide. The amount of hydrogen peroxide introduced is usually from 1 to 5 moles per mole alcohol, and good results often use 1.5 to 3 moles:mole alcohol. There is one further variation that can be employed. It is not necessary to introduce HBr as such into the reaction mixture, but instead it can be formed in situ by acid displacement, using a strong acid such as sulphuric acid and a bromide salt such as ammonium bromide.

It will be recognised that at the end of the reaction period there will be two phases when the hydrogen peroxide/HBr/Br$_2$ cycle is used, and that the aqueous phase will contain a very high proportion of the residual HBr/BR$_2$. Thus, after separation from the organic phase it is available for use subsequently with fresh alcohol and hydrogen peroxide. However, since on each cycle water is produced from hydrogen peroxide the aqueous phase inevitably becomes more dilute, so that is prudent to supplement the HBr concentration on each cycle or at least periodically.

Whilst it is desirable to have an aqueous phase present so as to reduce contact between HBr and the organics, especially the ketone, it is also desirable not to have too large an aqueous phase in that losses of product into it would thereby be encouraged. Thus, it is preferable to maintain the volume ratio of organic to aqueous phase within the range of 3:1 to 1:1, and particularly around 2:1.

The aqueous phase contains also the hydrogen peroxide, which is normally introduced as an aqueous solution having a concentration of at least 35% and preferably at least 50% w/w solution. To control the amount of added water, a concentration of above 70% w/w H$_2$O$_2$ would be usable, but its use is not necessary and on a large scale would be hindered by cost and transport difficulties. The hydrogen peroxide could be introduced in a variety of schemes varying from single shot at the start of the reaction to continuous addition throughout, always provided that the ratio of the organic compounds to hydrogen peroxide and water was never allowed to reach those ratios that are hazardous, ie not reach a combination of high organics plus high hydrogen peroxide but low water. Broadly speaking, it is desirable to bring into some degree of correspondence the rates at which bromine is generated and consumed. In practice, it is beneficial for part of the $H_2O_2$ to be added at the start and part progressively during the reaction, that is to say incremental addition at intervals or continuous addition.

It is by controlling the rate of introduction of hydrogen peroxide into the reaction mixture whilst employing a substoichiometric amount of HBr that improved selectivity to the non-bromine substituted ketone can be achieved, particularly in the case of the more reactive alcohols. Expressed as a general principle, under otherwise identical process conditions, the selectivity of the reaction products in favour of the ketone compared with bromine substituted products increases as the rate of introduction of hydrogen peroxide increases, ie as the period during which it is introduced decreases. Thus, the period of introduction is normally not longer than 40 minutes when oxidising any of the alcohols, although longer periods such as up 120 minutes may be tolerated for less reactive alcohols. The period is usually at least 5 minutes for the introduction of a stoichiometric amount of hydrogen peroxide for oxidising the more reactive alcohols and preferably not more than 20 minutes, whereas for the less reactive alcohols, consumption of the bromine generated is slower and thus it can be generated more slowly too, so that the period of introduction of $H_2O_2$ is often from 10 to 40 minutes.

When employed, the radiation illuminating the reaction has as its object the dissociation of bromine into bromine radicals. Thus, the effective radiation has a wavelength of not more than 600 nm. A significant proportion of useful radiation is available from lamps which have principal emissions in the range of 600 to 250nm. Some of the usefull lamps are described as daylight lamps, whilst other fall into the category of UV A or UV B emitters. It will be recognised that there is a relationship between radiation intensity and reaction rate and consequently also with reaction period, the more intense the radiation, the faster the rate and shorter the possible reaction period. The actual design of the reaction vessel is within the control of the process operator. Radiation lamps can for example be positioned above the surface of the reaction mixture and/or immersed within it. Alternatively or additionally the vessel can be provided with translucent ports through which the radiation is shone into the reaction mixture. Reflectors can be used to minimise radiation losses. In some instances, the illuminance will be selected in the range of $5 \times 10^4$ to $5 \times 10^6$ lux. Effective results have been obtained conveniently in the region of about $5 \times 10^5$ lux.

It will be recognised that by way of a modification of the present invention, it is possible introduce bromine itself into the reaction medium instead of generating it in situ by use of hydrogen peroxide and HBr for reaction with the less reactive alcohols, and provided that the mixture is appropriately irradiated, then under the same reaction conditions as described previously herein for such alcohols, a more selective product is obtained than would be if the inventive feature of irradiation were not effected, but under otherwise identical process conditions, the selectivity is not as great as when the bromine is generated in situ. Such a modification is retained within the broadest expression of the ambit of the present invention.

Including the period of introduction of hydrogen peroxide, the reaction period is normally selected within the range of 0.5 to 10 hours and in many instances is from 1 to 3.5 hours, so that the light exposure is often in the range of at least $1-5 \times 10^5$ lux-hours such as up to $5 \times 20^6$ lux hours. Obviously, greater light exposure (as measured in lux hours) is employable but at additional expenditure. As a matter of practice, it is desirable in order to obtain the highest alcohol conversion to allow the reaction to continue whilst bromine is present. Its presence can be monitored visually or automatically, by virtue of the distinctive colour it imparts to the aqueous phase and the colour loss signals the reaction end.

The temperature of the reaction mixture can be selected in the range of 5 to 70° C., but in order to take more fully advantage of the bromine radical reaction route it is preferable to suppress to some extent the competitive bromine reactions, which are believed possibly to be ionic in character, especially for less reactive alcohols, by maintaining a reaction temperature that is close to ambient, the preferred range being 15 to 35° C.

An advantageous combination of parameters for an irradiated reaction of a less reactive alcohol such as dichloro-propan-2-ol comprises use of a reaction temperature of around 25° C., up to 35° C. coupled with a reaction period varying from about 1.5 to about 3.5 hours, a hydrogen bromide to alcohol mole ratio of from 0.5:1 to 1.2:1, a hydrogen peroxide to alcohol mole ratio of about 1:1 to 1.2:1 introduced in the form of a 50-75% w/w aqueous solution and preferably during 10 to 40 minutes, the alcohol being present in an inert organic solvent, preferably a chloro alkane, at a concentration of around 10 to 30% w/v and the reaction mixture being a two phase system, the ratio of organic solvent to water (prior to introduction of any hydrogen peroxide) being about 8:1 to 3:1 v/v. A process so limited combines high yield of product from such an alcohol with high selectivity, thereby minimising variable process costs.

An advantageous combination of parameters for oxidation of a more reactive alcohol such as hexan-2-ol comprises use of a reaction temperature of around 25° C., up to 60° C. coupled with a reaction period varying from about 1.5 to about 3.5 hours, a hydrogen bromide to alcohol mole ratio of from 0.1:1 to 1:1, a hydrogen peroxide to alcohol mole ratio of about 1:1 to 1.2:1 introduced in the form of a 50-75% w/w aqueous solution during 5 to 20 minutes, the alcohol being present in an inert organic solvent, preferably a chloro alkane, at a concentration of around 10 to 30% w/v and the reaction mixture being a two phase system, the ratio of organic solvent to water (prior to introduction of any hydrogen peroxide) being about 8:1 to 3:1 v/v, the process being conducted in the presence or absence of irradiation at the discretion of the user.

The ketone product can be recovered from the reaction mixture by first separating the organic and aqueous phases and if desired the aqueous phase can also be washed with further volumes of organic solvent, and preferably the same as that employed in the reaction mixture. The organic phase can then be distilled, in some cases under reduced pressure with precipitation of the ketone, possibly continuing evaporation to dryness.

The aqueous phase, as has been described already can be immediately recycled, or more usually the required fraction of it can be recycled, preferably with its HBr concentration restored to its starting concentration.

The effects of employing in situ generated bromine as oxidant in the preferred manner of the instant invention can be seen to be first that it transforms the reagant from being a laboratory curiosity to a viable process and secondly substantially reduces the extent of effluent or other waste to be dealt with, as well of course as substantially improving the real cost of the process by reducing effluent handling, reducing by-product formation and losses of hydrogen bromide. Furthermore, the necessity of handling bromine is avoided.

Having described in general terms the instant invention, some specific embodiments will be provided by way of example only.

In each of Examples 1 to 15 and comparison CA, the reaction was carried out in a multi necked 200 ml glass flask equipped with stirrer, thermometer and inlet port through which reagent can be introduced. 1,3-dichloropropan-2-ol (DCP) was dissolved in an organic solvent, (100 mls, which was chloroform except for Ex 9 when it was dichloromethane) with agitation at 30° C. in the flask.

A solution of HBr was made by dissolving ammonium bromide and concentrated sulphuric acid in a mole ratio of 2:1 in water and this was introduced into the flask to provide the volume of water and mole ratio of HBr:DCP specified in the Table.

The reaction mixture was brought, where necessary, to the reaction temperature and the desired amount of aqueous hydrogen peroxide (70% w/w) was then introduced slowly and progressively into the flask with stirring over a period of 1.5 hours. During the remainder of the reaction period, no further peroxide was introduced, but the reaction continued to be stirred and maintained at the selected temperature. For those nominally carried out at 25° C., the temperature did range between 25 and 30° C. In Example 15, the reaction was terminated after 1 hour so that only about half of the intended amount of hydrogen peroxide had been introduced.

Throughout the reaction period except in comparison CA, the flask was irradiated by a daylight scpectrum lamp positioned about 25-30 cm away and shining a beam onto the mixture. The lamp employed was a Thorn Al/258 24 volt 250 watt lamp, having a nominal luminous flux of 8500 lumens.

At the end of the reaction period, the reaction mixture was cooled to ambient temperature and the lower organic phase was run off. The aqueous residue was then washed twice with its own volume of fresh organic solvent, usually chloroform, and the washings combined with the organic phase. Solvent was stripped off at reduced pressure yielding a solid product containing dichloroacetone (DCA), which was analysed by capillary gas chromatography.

The procedure was slightly different in Example 8, in that the aqueous phase consisted of the separated aqueous phase from Example 7 made up to its original volume concentration of HBr.

In comparison CA, the reaction was carried out without any illumination in a darkened room.

In Example 16, the same apparatus and procedure was employed with the exception that the aqueous phase (10mls) contained initially 0.1 mole bromine and neither sulphuric acid nor hydrogen peroxide was introduced at all. About half way through the reaction a further 10 mls of water was introduced making the total of 20 mls shown in the Table.

THE TABLE

| Example | 1 | 2 | 3 | 4 | 5 | 6 | 7 | 8 |
|---|---|---|---|---|---|---|---|---|
| Reaction Mixture | | | | | | | | |
| Solvent - mls | 100 | 100 | 100 | 100 | 100 | 100 | 100 | 100 |
| Water - mls | 5 | 15 | 30 | 50 | 100 | 15 | 30 | 30 |
| DCP - moles | 0.2 | 0.2 | 0.2 | 0.2 | 0.2 | 0.1 | 0.2 | 0.2 |
| ratio HBr:DCP | 0.25 | 0.5 | 1 | 1 | 1 | 1 | 1 | 1 |
| ratio $H_2O_2$:DCP | 1.1 | 1.1 | 1.1 | 1.1 | 1.1 | 2.2 | 1.1 | 1.1 |
| Reaction Conditions | | | | | | | | |
| Temp °C. | 60 | 60 | 60 | 60 | 60 | 60 | 60 | 60 |
| Period - hours | 3 | 3 | 3 | 2.5 | 2 | 2.5 | 3 | 3 |
| Reaction Product | | | | | | | | |
| conversion DCP % | 26 | 100 | 97 | 93 | 92 | 100 | 98 | 91 |
| Yield DCA % | 10 | 72 | 56 | 50 | 29 | 64 | 61 | 62 |
| Selectivity % | 40 | 72 | 58 | 53 | 31 | 64 | 63 | 68 |
| Example | 9 | 10 | 11 | 12 | 13 | 14 | 15 | CA | 16 |
| Reaction Mixture | | | | | | | | | |
| Solvent - mls | 100 | 100 | 100 | 100 | 100 | 100 | 100 | 100 | 100 |
| Water - mls | 30 | 30 | 15 | 20 | 20 | 40 | 4 | 50 | 20 |
| DCP - moles | 0.2 | 0.2 | 0.2 | 0.2 | 0.2 | 0.2 | 0.2 | 0.2 | 0.2 |
| ratio HBr:DCP | 1 | 1 | 0.5 | 1 | 1 | 2 | 0.2 | 1 | * |
| ratio $H_2O_2$:DCP | 1.1 | 1 | 1 | 1 | 1 | 1 | 1 | 1.1 | — |
| Reaction Conditions | | | | | | | | | |
| Temp °C. | 40 | 30 | 20 | 20 | 25 | 25 | 25 | 60 | 25 |
| Period - hours | 2.5 | 4 | 3 | 4.5 | 3.5 | 3 | 1 | 3.5 | 3.5 |
| Reaction Product | | | | | | | | | |
| Conversion DCP % | 100 | 96 | 97 | 93 | 97 | 95 | 40 | 0 | 94 |
| Yield DCA % | 70 | 77 | 50 | 71 | 83 | 54 | 6 | 0 | 74 |
| Selectivity % | 70 | 80 | 62 | 76 | 86 | 57 | 14 | 0 | 78 |

From the Table, a comparison between Examples 1 and 15 on the one hand and Examples 3 et seq on the other shows clearly that a relatively low mole ratios of HBr:DCP, the conversion of DCP falls away substantially, so that a mole ratio of HBr:DCP approaching or exceeding 0.5:1 is advantageous. It can also be seen from Example 14, that if a relatively high mole ratio of HBr:DCP is employed the selectivity of DCA (dichloroacetone) production can be impaired to some extent.

The Table clearly demonstrates that changes in the relative volumes of the organic and aqueous phases of the reaction mixture can significantly affect the selectivity of the reaction. A comparison of Examples 1 through to 5 shows clearly that the presence of about 15 mls water per 100 mls organic solvent, plus that present in and generated from added hydrogen peroxide gave the best selectivity in the series, with the presence of 30 mls being second best. Subsequent Examples 6 to 9 and 11 to 13 confirm that optimum selectivity was found at about 2 mls added water per 100 mls solvent.

The Table shows in Example 16 that bromine can be used without regeneration and can produce as product DCA in good yield and high selectivity.

The Table demonstrates that reaction temperatures in the region of 20 to 60° C., can be employed in the production of DCA, and in particular that greater selectivity is achieved at a reaction temperature at or around ambient, and especially about 25° C. Furthermore, the Table shows that the reaction rate changes relatively little with change in tempertaure.

Most importantly, and finally, the comparison experiment CA shows that the oxidation reaction does not proceed in the absence of irradiation which is capable of generating bromine free radicals.

In Example 17, the apparatus and general procedure of the preceding Examples were followed for the oxidation of 1,3-dibromopropan-2-ol (0.046 moles), employing a reaction mixture containing water (10mls), $NH_4Br$ (0.046 moles) and $H_2SO_4$ (0.022 moles) and $CHCl_3$ (25g). Hydrogen peroxide (0.046 moles, as 65% w/w solution) was introduced into the irradiated vessel over a period of 1 hour and the reaction continued at ambient temperature, i.e. about 22 to 25° C., until all the hydrogen peroxide had been consumed, which was after a further 4 hours. The product was recovered and analysed as in the preceding Examples and it was found that 99% of the alcohol had been consumed, with an 85% molar selectivity to 1,3-dibromoacetone.

In Example 18, the same apparatus, reagents, amounts, conditions and procedure of Example 17 was followed but starting with benzoin and using 75g $CHCl_3$. The hydrogen peroxide was introduced over 30 minutes and the subsequent reaction time was 7 hours. The conversion of benzoin to benzil was approximately 94%, and selectivity was about 100%.

In Example 19, the apparatus and general procedure of Examples 1 to 17 were followed for the oxidation of 1,2,3-trichloropropan-2-ol (0.0616 moles), employing a reaction mixture containing water (6.8mls), $NH_4Br$ (0.046 moles) and $H_2SO_4$ (0.022 moles) and $CHCl_3$ (25g). Hydrogen peroxide (0.0855 moles, as 65% w/w solution) was introduced into the irradiated vessel over a period of 30 minutes and the reaction continued at ambient temperature, i.e. about 22 to 25° C., until all the hydrogen peroxide had been consumed, which was after a further 7 hours. The product was recovered and anlysed as in the preceding Examples and it was found that 8.0g of a product was obtained containing both trichloroacetone and dichlorobromoacetone.

In a similar manner and apparatus, in Example 20, cyclohexanol (0.2 moles) $NH_4Br$ (0.2 moles) $H_2SO_4$ (0.1 moles) $H_2O$ (30 mls) and $CHCl_3$ (100 mls) were charged to an reaction vessel irradiated as before, and $H_2O_2$ (0.22 moles, 65% w/w solution) was introduced with stirring over 20 minutes, during which time the reaction mixture fell from an initial temperature of 38° C. to a continuing reaction temperature of about 19° C. during the next hour or so. Analysis showed that 88% of the alcohol had been consumed, with a molar selectivity of 68.5% to cyclohexanone and 18% to 2-bromocyclohexanone.

In Example 21, Example 20 was repeated, but the $H_2O_2$ was introduced over a period of 36 minutes instead of 20 minutes. The consumption of alcohol had fallen to 71.6%, the proportion of the desired cyclohexanone in the products had fallen to 62% and the undesired bromocyclohexanone had risen to 31%. By comparison with Example 20, it will seen that the change in the rate of introduction of hydrogen was significant and that the better result was achieved with the faster rate. The same trend was observed when the period of $H_2O_2$ introduction was increased first to 70 minutes (in the absence of irradiation) and to 140 minutes with irradiation, the consumptions falling respectively to 70 and 59% and the desired proportion to 48 and 39%.

In Example 22, the procedure of Example 20 was followed on the same scale, except for employing phenyl-1-ethanol insyead of cyclohexanol, introducing the $H_2O_2$ over 30 minutes and maintaining the reaction mixture of about 60° C during a total reaction period of 55 minutes. 100% consumption of the alcohol was achieved with 77.3% selectivity to the ketone.

In Example 23, the procedure of Example 22 was followed except for employing only half as much HBr, ie a mole ratio of 0.5:1 HBr:alcohol, an introduction period of 25 minutes and a total reaction period of 90 minutes. Once again 100 alcohol consumption was observed, and the selectivity of ketone production had increased to 89.3%. Phenyl is not a strongly electronegative substituent, so that the alcohol a is reasonably reactive and thus the control of residual HBr during the reaction, as shown by comparing Examples 22 and 23 is important.

In Example 24 the procedure of Example 20 was followed, but employing hexan-2-ol instead of cyclohexanol, and at holf scale. The hydrogen peroxide was introduced over 16 minutes and the reaction permitted to continue for a total of 228 minutes. The consumption of alcohol was 96% and selectivity to the ketone was 100%. This Example demonstrates that for an alcohol of intermediate to high reactivity, a very good selectivity is achievable when the reaction mixture is illuminated with radiation that dissociated bromine into radicals whilst employing a mole ratio of HBr:alcohol of about 1:1 and introducing the hydrogen peroxide quickly.

In Example 25, Example 24 was repeated, but using twice as much $CHCl_3$, slightly shortening the $H_2O_2$ introduction period to 14 minutes and significantly effecting the reaction in a dark reaction vessel into which bromine-dissociating radiation could not penetrate. The reaction period was increased to 390 minutes to permit the reaction to procede until all the bromine generated had been consumed. It was found that the consumption of alcohol had stayed about the same, 97%, but that selectivity had fallen to 80.7% ketone. This demonstrates that for such an alcohol of intermediate reactivity, the presence of absence of appropriate radiation is significant.

In Example 26, Example 25 was repeated, but employing only 1/10th the amount of HBr, ie in a mole ratio to the alcohol of 0.1:1. It was observed that the extent of alcohol consumption fell to 77% but the selectivity to ketone increased to 89%. This shows the amount of HBr in the reaction mixture is significant as regards both reactivity and selectivity for an alcohol of intermediate reactivity.

We claim:

1. In a process for the oxidation of a secondary alcohol to a ketone by reacting it with at least a stoichiometric amount of bromine the improvement which comprises employing, regenerating and reemploying in a reaction mixture a substoichiometric amount of hydrogen bromide in a two step cycle in which in one step of said cycle bromine is generated in situ by a reaction between the bromide and hydrogen peroxide and in the second step of said cycle bromine is consumed by reaction with the alcohol with consequential regeneration of bromide; and the process further comprising employing at least one of features (a) and (b), the selection of features (a) and (b) being dependent upon the inherent reactivity of the alcohol with bromine, (a) being essential when said inherent reactivity of the alcohol is deactivated and (b) becoming progressively essential as said inherent reactivity of the alcohol to be oxidised becomes comparatively more active, feature (a) comprising irradiating the reaction mixture with radiation that is capable of dissociating bromine into free radicals, and feature (b) comprising the use of a comparatively rapid rate of introduction of the hydrogen peroxide in conjunction with a comparatively low sub-stoichiometric mole ratio of HBr: alcohol in the reaction mixture, whereby the selectivity of the reaction is improved.

2. A process according to claim 1 characterised in that the alcohols are substituted on an adjacent carbon atom to the hydroxyl-substituted carbon atom by at least one electronegative group and the reaction mixture is irradiated in accordance with feature (a).

3. A process according to claim 2 characterised in that the electronegative group is a chloro group.

4. A process according to claim 2 characterised in that the alcohol is a halopropanol.

5. A process according to claim 4 characterised in that the alcohol is 1,3-dichloropropan-2-ol, 1,1,1-trichloropropan-2-ol or 1,3-dibromopropan-2-ol.

6. A process according to claim 2 characterised in that the radiation employed has a wavelength of not longer than 600 nm.

7. A process according to claim 6 characterised in that the radiation employed has a wavelength in the range of from 250 to 600nm.

8. A process according to claim 2 characterised in that the radiation is shone into the reaction mixture at an illuminance of $5 \times 10^4$ to $5 \times 10^6$ lux.

9. A process according to claim 2 characterised in that the reaction mixture is exposed to $1.5 \times 10^5$ to $5 \times 10^6$ lux-hours of radiation.

10. A process according to claim 2 characterised in that the radiation employed has a wavelength in the range of from 250 to 600nm which is shone into the reaction mixture at an illuminance of $5 \times 10^4$ to $5 \times 10^6$ lux in a total amount of $1.5 \times 10^5$ to $5 \times 10^6$ lux-hours of radiation.

11. A process according to claim 2 characterized in that the HBr:alcohol mole ratio is selected in the range of 0.4:1 to 1.5:1.

12. A process according to claim 2 characterised in that the reaction temperature is in the range of 15 to 35° C.

13. A process according to claim 1 characterised in that the reaction is effected at a temperature of from 5 to 70° C.

14. A process according to claim 1 characterised in that the alcohol is relatively free from deactivation and in accordance with feature (b) the mole ratio of HBr: alcohol in the mixture is selected in the range of 0.05:1 to 1:1.

15. A process according to claim 14 characterised in that in accordance with feature (b) the hydrogen peroxide is introduced into the reaction mixture during a period of from 5 to 20 minutes.

16. A process according to claim 14 characterised in that the amount of hydrogen peroxide introduced is from 1 to 1.2 moles per mole of alcohol.

17. A process according to claim 14 characterised in that the alcohol is selected from saturated aliphatic or cycloaliphatic alcohols that are either unsubstituted or substituted by one or more alkyl or aryl hydrocarbon substituents or benzoin.

18. A process according to claim 17 characterised in that the alcohol is selected from cyclohexanol, hexan-2-ol, octan-2-ol, 1-phenyl ethanol and benzoin.

19. A process according to claim 18 characterised in that the hydrogen peroxide is introduced into the reaction mixture during a period of from 5 to 20 minutes in a total amount of from 1 to 1.2 moles per mole of alcohol.

20. A process according to claim 1 characterised in that the hydrogen peroxide:alcohol mole ratio is selected in the range of 1:1 to 5:1.

21. A process according to claim 1 characterised by employing a two-phase reaction medium, one phase comprises a relatively a polar solvent and the other phase comprises a relatively non-polar solvent whereby HBr/bromide is retained primarily in the relatively polar phase and the alcohol and the ketone are retained primarily in the relatively non-polar phase, thereby minimising their interaction.

22. A process according to claim 21 characterised in that the non-polar solvent is selected from liquid hydrocarbons and halogenated hydrocarbons.

23. A process according to claim 22 characterised in that the non-polar solvent is at least one selected from the group consisting of chloroform, ethylene dichloride and dichloromethane.

24. A process according to claim 21 characterised in that the alcohol is present at a concentration of 100 to 300 gpl in the non-polar solvent.

25. A process according to claim 21 characterised in that the volume ratio of non-polar to polar phases is in the range of 3:1 to 1:1.

26. A process according to claim 1 characterised in that the hydrogen peroxide is introduced in the form of a 35% to 70% w/w solution in water.

* * * * *